United States Patent
Matsumoto (10) Patent No.: US 10,416,433 B2
(45) Date of Patent: Sep. 17, 2019

(54) CELL IMAGE ACQUISITION DEVICE, METHOD, AND PROGRAM

(71) Applicant: FUJIFILM Corporation, Tokyo (JP)

(72) Inventor: Tsuyoshi Matsumoto, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 4 days.

(21) Appl. No.: 15/251,819

(22) Filed: Aug. 30, 2016

(65) Prior Publication Data
US 2016/0370569 A1 Dec. 22, 2016

Related U.S. Application Data

(63) Continuation of application No. PCT/JP2015/051066, filed on Jan. 16, 2015.

(30) Foreign Application Priority Data

Mar. 4, 2014 (JP) ................. 2014-041688

(51) Int. Cl.
*G06K 9/00* (2006.01)
*G02B 21/36* (2006.01)
(Continued)

(52) U.S. Cl.
CPC ........... *G02B 21/365* (2013.01); *C12M 41/36* (2013.01); *C12M 41/46* (2013.01); *C12M 41/48* (2013.01);
(Continued)

(58) Field of Classification Search
None
See application file for complete search history.

(56) References Cited

U.S. PATENT DOCUMENTS

2001/0033414 A1* 10/2001 Yahiro ................. B01L 3/5085
359/383
2002/0086347 A1* 7/2002 Johnson ............. A61B 5/02007
435/40.5
(Continued)

FOREIGN PATENT DOCUMENTS

JP 8-287261 A 11/1996
JP 2011-229409 A 11/2011
(Continued)

OTHER PUBLICATIONS

Sammak, P. J., Abraham, V., Ghosh, R., Haskins, J., Jane, E., Petrosko, P., . . . & Mangoubi, R. (2008). High content analysis of human embryonic stem cell growth and differentiation. High Content Screening: Science, Techniques, and Applications: John Wiley & Sons, Inc, 205-224.*
(Continued)

*Primary Examiner* — Samah A Beg
(74) *Attorney, Agent, or Firm* — Birch, Stewart, Kolasch & Birch, LLP (57) ABSTRACT

There is provided a cell image acquisition device, method, and a non-transitory computer readable recording medium recorded with a program to reduce the amount of data to be processed and stored by limiting a target region in a colony region when imaging a cell colony. There are included: a maturity information acquisition unit 22 that acquires information regarding the maturity of cells being cultured; a colony region specifying unit 21 that acquires a cell image by imaging the cells at a first magnification and specifies a colony region of the cells in the cell image; a target region determination unit 23 that determines a target region in the colony region of the cells based on the information regarding the maturity; and a high magnification image acquisition unit 24 that acquires a high magnification image by imaging
(Continued)

the target region at a second magnification that is higher than the first magnification.

22 Claims, 7 Drawing Sheets

(51) Int. Cl.
```
G01N 15/14      (2006.01)
G02B 21/00      (2006.01)
G02B 21/08      (2006.01)
G02B 21/14      (2006.01)
C12M 1/34       (2006.01)
C12M 1/36       (2006.01)
G06K 9/46       (2006.01)
G01N 15/10      (2006.01)
G01N 15/00      (2006.01)
```
(52) U.S. Cl.
CPC ..... *G01N 15/1475* (2013.01); *G02B 21/0004* (2013.01); *G02B 21/086* (2013.01); *G02B 21/14* (2013.01); *G06K 9/0014* (2013.01); *G06K 9/00127* (2013.01); *G06K 9/00134* (2013.01); *G06K 9/4604* (2013.01); *G01N 15/1463* (2013.01); *G01N 2015/0065* (2013.01); *G01N 2015/1006* (2013.01)

(56) References Cited

U.S. PATENT DOCUMENTS

| | | | | |
|---|---|---|---|---|
| 2005/0058330 A1* | 3/2005 | Mitsuhashi | ............ | G06Q 50/22 382/128 |
| 2007/0014459 A1* | 1/2007 | Palmer | ................. | G06T 7/0012 382/128 |
| 2009/0159814 A1 | 6/2009 | Maiya | | |
| 2010/0002929 A1* | 1/2010 | Sammak | ........... | G06K 9/00127 382/133 |
| 2010/0128961 A1* | 5/2010 | Kalusche | ........... | G01N 15/1475 382/133 |
| 2010/0219353 A1* | 9/2010 | Akiyoshi | ........... | G01N 21/6458 250/459.1 |
| 2012/0013728 A1 | 1/2012 | Matsuo | | |
| 2012/0087556 A1* | 4/2012 | Dai | ...................... | G06K 9/0014 382/128 |
| 2012/0120302 A1* | 5/2012 | Kiyota | .................... | G02B 7/38 348/345 |
| 2012/0122143 A1* | 5/2012 | Mimura | ................. | C12M 41/14 435/29 |
| 2012/0134571 A1 | 5/2012 | Ito et al. | | |
| 2013/0188033 A1* | 7/2013 | Oda | ................... | G01N 15/1463 348/79 |
| 2014/0168402 A1* | 6/2014 | Fuller | ................. | G02B 21/361 348/79 |
| 2014/0307226 A1* | 10/2014 | Lathrop | ............... | A61B 3/0025 351/206 |
| 2016/0069903 A1* | 3/2016 | Lakadamyali | ..... | G01N 33/6875 435/7.1 |
| 2016/0160170 A1* | 6/2016 | Matsubara | ............. | C12M 41/36 435/287.1 |
| 2016/0161464 A1* | 6/2016 | Tsujimoto | .............. | C12M 41/36 435/34 |
| 2016/0163049 A1* | 6/2016 | Matsubara | ............. | C12M 41/36 382/133 |
| 2016/0252719 A1* | 9/2016 | Liu | .................... | G01N 33/4833 348/49 |
| 2016/0335767 A1* | 11/2016 | Matsumoto | ........... | G06T 7/0012 |
| 2016/0369223 A1* | 12/2016 | Matsumoto | ............ | G02B 21/14 |
| 2016/0370569 A1 | 12/2016 | Matsumoto | | |
| 2017/0161468 A1* | 6/2017 | Matsumoto | ........... | G06F 19/366 |
| 2017/0166948 A1* | 6/2017 | Matsumoto | .............. | C12Q 1/02 |
| 2017/0191021 A1* | 7/2017 | Wakui | ...................... | C12N 5/10 |

FOREIGN PATENT DOCUMENTS

| | | | | | |
|---|---|---|---|---|---|
| JP | 2011-239778 | A | | 12/2011 | |
| JP | 2012-2949 | A | | 1/2012 | |
| JP | 2012002949 | A | * | 1/2012 | ........... G02B 21/365 |
| JP | 2012-19748 | A | | 2/2012 | |
| JP | 2013-201909 | A | | 10/2013 | |
| JP | 2014-18184 | A | | 2/2014 | |
| JP | 2014018184 | A | * | 2/2014 | ......... G06K 9/00147 |
| JP | 2015-165785 | A | | 9/2015 | |
| WO | WO 2007/142339 | A1 | | 12/2007 | |
| WO | WO 2009/125547 | A1 | | 10/2009 | |
| WO | WO 2010/128670 | A1 | | 11/2010 | |
| WO | WO 2011/013319 | A1 | | 2/2011 | |
| WO | WO 2011/016189 | A1 | | 2/2011 | |

OTHER PUBLICATIONS

International Search Report, issued in PCT/JP2015/051066, PCT/ISA/210, dated Apr. 14, 2015.
Written Opinion of the International Searching Authority, issued in PCT/JP2015/051066, PCT/ISA/237, dated Apr. 14, 2015.
English Translation of International Preliminary Report on Patentability (including PCT/IB/373 and PCT/ISA/237) for PCT/JP2015/051066, dated Sep. 6, 2016.
Japanese Notification of Reasons for Refusal dated Feb. 28, 2017, for corresponding Japanese Application No. 2014-041688, including English translation.
Japanese Office Action, dated Aug. 8, 2017, for corresponding Japanese Application No. 2014-041688, along with an English machine translation.
The Japanese Decision of Refusal, dated Mar. 27, 2018, for corresponding Japanese Application No. 2014-041688, with an English machine translation.
Japanese Office Action, dated Mar. 19, 2019, for corresponding Japanese Application No. 2014-41688, with an English translation.
Japanese Office Action, dated Apr. 2, 2019, for corresponding Japanese Application No. 2018-120292, with an English translation.

* cited by examiner

| TYPE OF CELL | CULTURE CONDITIONS | CULTURE PERIOD | FOCUS SEARCH INITIAL POSITION IN CENTRAL PORTION (OFFSET AMOUNT FROM BOTTOM) | FOCUS SEARCH INITIAL POSITION IN PERIPHERAL PORTION (OFFSET AMOUNT FROM BOTTOM) |
|---|---|---|---|---|
| iPS | CONDITIONS A | EARLY STAGE | SMALL | SMALL |
| | | MIDDLE STAGE | LARGE | SMALL |
| | | LATE STAGE | SMALL | SMALL |
| | CONDITIONS B | EARLY STAGE | SMALL | SMALL |
| | | MIDDLE STAGE | LARGE | SMALL |
| | | LATE STAGE | LARGE | LARGE |
| ES | CONDITIONS A | EARLY STAGE | ... | ... |
| | | MIDDLE STAGE | | |
| | | LATE STAGE | | |
| | CONDITIONS C | EARLY STAGE | | |
| | | MIDDLE STAGE | | |
| | | LATE STAGE | | |

US 10,416,433 B2

CELL IMAGE ACQUISITION DEVICE, METHOD, AND PROGRAM

CROSS-REFERENCE TO RELATED APPLICATIONS

This application is a Continuation of PCT International Application No. PCT/JP2015/051066 filed on Jan. 16, 2015, which claims priority under 35 U.S.C § 119(a) to Japanese Patent Application No. 2014-041688 filed on Mar. 4, 2014. Each of the above application(s) is hereby expressly incorporated by reference, in its entirety, into the present application.

BACKGROUND OF THE INVENTION

1. Field of the Invention

The present invention relates to a cell image acquisition device, method, and a non-transitory computer readable recording medium recorded with a program for acquiring a high magnification image by imaging a target region in a cell colony at high magnification.

2. Description of the Related Art

Conventionally, a method of imaging stem cells such as ES cells or iPS cells, differentiation-induced cells, or the like using a microscope or the like and determining the culture state of cells by ascertaining the features of the image has been proposed.

In order to determine the culture state of cells based on the features of the image captured by imaging the cells as described above, a low magnification image is acquired first by imaging cells at low magnification, a target region that needs to be particularly focused upon in the low magnification image is then specified, a high magnification image is acquired by imaging the target region at high magnification, and the high magnification image is observed. Thereby, it is possible to recognize more detailed features of the cells.

For example, WO2010/128670A and WO2009/125547A have proposed a method of imaging a fertilized embryo being cultured at high magnification. In addition, JP2011-239778A and JP2011-229409A have proposed imaging a position in a vessel, which is designated by the user, at a designated magnification based on management data regarding the culture.

SUMMARY OF THE INVENTION

Here, for example, in the case of culturing stem cells, the form of a stem cell colony changes according to the culture period. Specifically, for example, in the early stage of culture, undifferentiated cells are uniformly distributed in a colony region. However, as the culture progresses, differentiation starts in a peripheral portion of the colony region so that differentiated cells are distributed in the peripheral portion.

That is, in the early stage of culture, observation may be performed focusing on the central portion of the colony region. However, when the culture has progressed, it is necessary to focus on a peripheral portion of the colony region in order to recognize the degree of differentiation.

For example, in the case of imaging the entire area of a stem cell colony at high magnification according to such a change in form of the stem cell colony, it is necessary to perform high magnification imaging for a plurality of regions obtained by dividing the entire area of the stem cell colony. Accordingly, the measurement time becomes very long. In addition, the data amount of an image captured at high magnification becomes enormous.

WO2010/128670A and WO2009/125547A have proposed imaging only individual fertilized embryos, and there is no proposal about imaging of a cell colony. Also in JP2011-239778A and JP2011-229409A, only imaging a predetermined observation position in a vessel based on the management data is disclosed, and there is no proposal about the above-described imaging according to the change in form of a cell colony.

In view of the aforementioned problems, it is an object of the present invention to provide a cell image acquisition device, method, and a non-transitory computer readable recording medium recorded with a program capable of reducing the amount of data to be processed and stored by appropriately limiting a target region, which is to be imaged at high magnification, in a colony region according to the change in form of the colony region when imaging a cell colony.

A cell image acquisition device of the present invention comprises: a maturity information acquisition unit that acquires information regarding maturity of cells being cultured; a colony region specifying unit that acquires a cell image by imaging the cells at a first magnification and specifies a colony region of the cells in the cell image; a target region determination unit that determines a target region in the colony region of the cells based on the information regarding the maturity; and a high magnification image acquisition unit that acquires a high magnification image by imaging the target region at a second magnification that is higher than the first magnification.

In the cell image acquisition device of the present invention described above, the target region determination unit may determine the target region as being at a position that changes with a stage of the maturity of the cells.

The target region determination unit may determine a region, which is inferred to be highly likely to differentiate due to maturation of the cells, as the target region.

The target region determination unit may determine a central portion in the colony region as the target region in a case where the maturity of the cells is an early stage, and may determine a peripheral portion in the colony region as the target region in a case where the maturity of the cells is a middle stage that is a stage in which the early stage has progressed.

The target region determination unit may determine a central portion in the colony region as the target region in a case where the maturity of the cells is a late stage that is a stage in which the middle stage has progressed.

The target region determination unit may determine a region including an edge of the colony region as the target region in a case where a stage of the maturity is a stage of an expanding growth phase set in advance.

As the information regarding the maturity, it is possible to acquire information regarding a culture period of the cells.

The maturity information acquisition unit may acquire the information regarding the maturity by analyzing image information of the colony region of the cells in the cell image.

As the information regarding the maturity, it is possible to acquire information regarding a shape or a size of the colony region of the cells.

The target region determination unit may determine a target region in the colony region of the cells based on the information regarding the maturity and culture conditions of the cells.

A cell image acquisition method of the present invention using the cell image acquisition device comprises: acquiring information regarding maturity of cells being cultured; acquiring a cell image by imaging the cells at a first magnification and specifying a colony region of the cells in the cell image; determining a target region in the colony region of the cells based on the information regarding the maturity; and acquiring a high magnification image by imaging the target region at a second magnification that is higher than the first magnification.

A non-transitory computer readable recording medium recorded with a cell image acquisition program of the present invention causes a computer to function as the cell image acquisition device comprising: a maturity information acquisition unit that acquires information regarding maturity of cells being cultured; a colony region specifying unit that acquires a cell image by imaging the cells at a first magnification and specifies a colony region of the cells in the cell image; a target region determination unit that determines a target region in the colony region of the cells based on the information regarding the maturity; and a high magnification image acquisition unit that acquires a high magnification image by imaging the target region at a second magnification that is higher than the first magnification.

According to the cell image acquisition device, method, and a non-transitory computer readable recording medium recorded with a program of the present invention, the information regarding the maturity of the cells being cultured is acquired, a target region in the colony region of the cells is determined based on the information regarding the maturity, and the high magnification image is acquired by imaging the determined target region at high magnification. Therefore, since it is possible to appropriately limit the target region according to the change in form of the colony region, it is possible to reduce the amount of data to be processed and stored.

DESCRIPTION OF THE PREFERRED EMBODIMENTS

Figure 1:
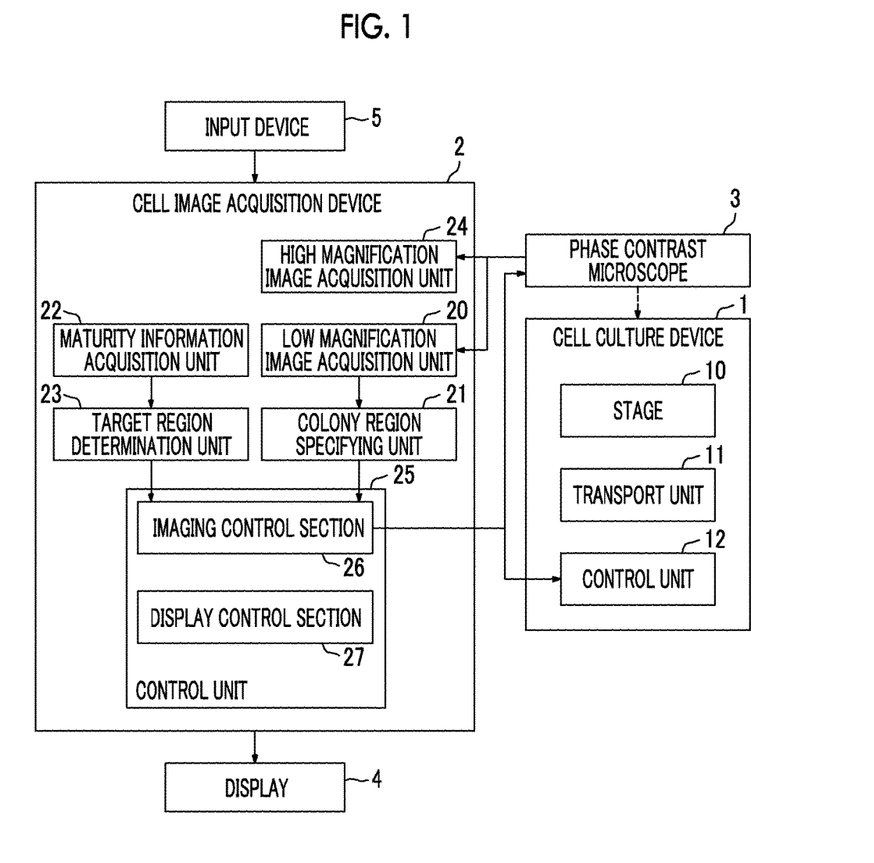
FIG. 1 is a block diagram showing the schematic configuration of a stem cell culture observation system using an embodiment of a cell image acquisition device of the present invention.

Hereinafter, a cell culture observation system using an embodiment of a cell image acquisition device, method, and a non-transitory computer readable recording medium recorded with a program of the present invention will be described in detail with reference to the diagrams. FIG. 1 is a block diagram showing the schematic configuration of a cell culture observation system.

As shown in FIG. 1, the cell culture observation system includes a cell culture device 1, a cell image acquisition device 2, a phase contrast microscope 3, a display 4, and an input device 5.

The cell culture device 1 is a device for culturing cells. As cells to be cultured, for example, there are pluripotent stem cells such as iPS cells, ES cells, or STAP cells, cells of nerves, skin, or liver that are differentiation-induced from stem cells, and cancer cells. In the cell culture device 1, a plurality of culture vessels are housed in which stem cells to be cultured are seeded on a culture medium. The cell culture device 1 includes a stage 10, a transport unit 11, and a control unit 12.

On the stage 10, a culture vessel to be imaged by the phase contrast microscope 3 is placed. The transport unit 11 selects a culture vessel to be imaged from a plurality of culture vessels housed in a predetermined position in the cell culture device 1, and transports the selected culture vessel to the stage 10. The control unit 12 controls the entire cell culture device 1, and controls not only the operation of the stage 10 or the transport unit 11 but also environmental conditions, such as the temperature, humidity, and $CO_2$ concentration in the cell culture device 1. As the configuration for adjusting the temperature, humidity, and $CO_2$ concentration, it is possible to use a known configuration.

Figure 2:
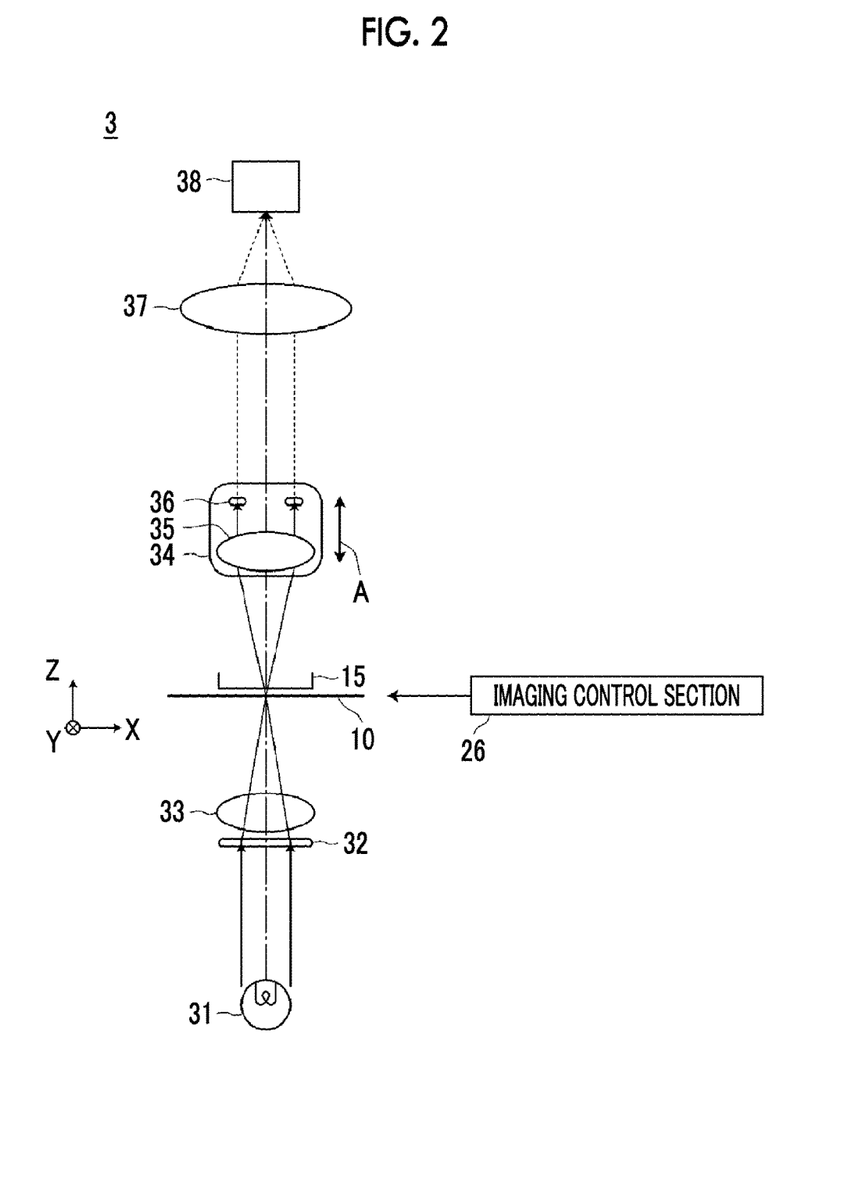
FIG. 2 is a diagram showing the schematic configuration of a phase contrast microscope.

The phase contrast microscope 3 captures a phase image of cells within the culture vessel placed on the stage 10. FIG. 2 is a diagram showing the schematic configuration of the phase contrast microscope 3. As shown in FIG. 2, the phase contrast microscope 3 includes: a white light source 31 which emits white light; a slit plate 32 which has a ring-shaped slit, on which the white light emitted from the white light source 31 is incident, and which emits ring-shaped illumination light; and an objective lens 33 on which the ring-shaped illumination light emitted from the slit plate 32 is incident and which emits the incident ring-shaped illumination light to cells in a culture vessel 15 placed on the stage 10.

In addition, a phase difference lens 34, an imaging lens 37, and an imaging element 38 are provided on the opposite side to the white light source 31 with respect to the stage 10.

The phase difference lens 34 includes an objective lens 35 and a phase plate 36. The phase plate 36 is configured by forming a phase ring on a transparent plate that is transparent for the wavelength of the ring-shaped illumination light. In addition, the size of the slit of the slit plate 32 described above and the phase ring are in the conjugate relationship.

The phase ring is configured by forming a phase film, which shifts the phase of incident light by ¼ wavelength, and a dimming filter for dimming the incident light in a ring shape. Direct light incident on the phase difference lens 34 is condensed by the objective lens 35, and is transmitted through the phase ring. As a result, the phase of the direct light is shifted by ¼ wavelength, and the brightness is weakened. On the other hand, most of the diffracted light diffracted by the cells in the culture vessel 15 passes through the transparent plate of the phase plate, and the phase and the brightness are not changed.

The phase difference lens 34 is moved in the arrow A direction shown in FIG. 2 by a driving mechanism (not shown). A focus position is changed by such movement of the phase difference lens 34, so that the focus control is performed. The driving mechanism moves the phase difference lens 34 based on the focus control signal output from an imaging control section 26 of the cell image acquisition device 2.

In addition, the phase contrast microscope 3 of the present embodiment is configured such that a plurality of phase difference lenses 34 having different magnifications are replaceable. For the replacement of the phase difference lens 34, automatic replacement may be performed according to an instruction input from the user, or manual replacement may be performed by the user.

In the present embodiment, low magnification imaging for macro observation and high magnification imaging for detailed observation are performed. The 1× to 4× phase difference lens 34 is used at the time of low magnification imaging, and 10× to 20× phase difference lens 34 is used at the time of high magnification imaging. However, the low magnification imaging and the high magnification imaging may be performed with relatively different magnifications, and are not limited to such magnification.

Direct light and diffracted light that are transmitted through the phase difference lens 34 are incident on the imaging lens 37, and an image of these light beams is formed on the imaging element 38. The imaging element 38 captures a phase image of cells by performing photoelectric conversion of the image formed by the imaging lens 37. As the imaging element 38, a charge-coupled device (CCD) image sensor, a complementary metal-oxide semiconductor (CMOS) image sensor, or the like can be used.

Although the phase contrast microscope 3 is used as an imaging device in the present embodiment, microscopes capable of changing to other optical magnification may be used. For example, a differential interference microscope may be used.

Referring back to FIG. 1, the cell image acquisition device 2 includes a low magnification image acquisition unit 20, a colony region specifying unit 21, a maturity information acquisition unit 22, a target region determination unit 23, a high magnification image acquisition unit 24, and a control unit 25. The control unit 25 includes the imaging control section 26 and a display control section 27.

The cell image acquisition device 2 is formed by installing an embodiment of a cell image acquisition program of the present invention in a computer.

The cell image acquisition device 2 includes a central processing unit, a semiconductor memory, a hard disk, and the like, and an embodiment of the cell image acquisition program is installed in the hard disk. When the program is executed by the central processing unit, the low magnification image acquisition unit 20, the colony region specifying unit 21, the maturity information acquisition unit 22, the target region determination unit 23, the high magnification image acquisition unit 24, the imaging control section 26, and the display control section 27 shown in FIG. 1 operate.

The low magnification image acquisition unit 20 acquires a cell image obtained by performing the above-described low magnification imaging by the phase contrast microscope 3. As the low magnification image acquired by the low magnification image acquisition unit 20, one image may be acquired by imaging one cell colony, or a group of a plurality of images may be acquired by dividing one cell colony into a plurality of rectangular divided regions. In addition, a plurality of cell colonies may be included in one image.

The low magnification image acquisition unit 20 stores identification information for identifying a cell colony and a low magnification image so as to match each other. For example, in a case where one cell colony is captured as one low magnification image, identification information of the cell colony and the low magnification image are stored so as to match each other in a one-to-one manner. In a case where one cell colony is captured as low magnification images of a plurality of divided regions, identification information of the cell colony and the low magnification images of the plurality of divided regions are stored so as to match each other. In addition, in a case where a plurality of cell colonies are captured as one low magnification image, identification information of each of the cell colonies and one low magnification image are stored so as to match each other.

By managing the identification information of each cell colony and a low magnification image so as to match each other as described above, for example, when a user inputs the identification information of the cell colony through the input device 5, it is possible to immediately read and display the low magnification image matched with the identification information.

The colony region specifying unit 21 specifies a position of a cell colony region in the low magnification image acquired by the low magnification image acquisition unit 20. As a method of specifying a cell colony region, for example, it is desirable to specify the position of a cell colony by converting a low magnification image into a binary image and then automatically extracting a cell colony region by template matching or the like. For the automatic extraction of a cell colony region, other known methods may be used without being limited to the method described above.

In addition, without being limited to the automatic extraction, a low magnification image may be displayed on the display 4 by the display control section 27, the user may designate a cell colony region in the low magnification image using the input device 5, and the colony region specifying unit 21 may acquire position information, such as the designated coordinates.

The maturity information acquisition unit 22 acquires information regarding the maturity of cells. The information regarding the maturity acquired by the maturity information acquisition unit 22 is used when determining a target region in the cell colony region in the target region determination unit 23. The target region is an imaging target region in the high magnification imaging described above.

In the present embodiment, the maturity of cells is divided into three stages of an early stage of culture, a middle stage of culture, a late stage of culture, and information regarding the maturity of cells is acquired by the maturity information acquisition unit 22, thereby acquiring a stage to which the maturity of cells to be imaged belongs.

The reason why the maturity of cells is divided into the early stage of culture, the middle stage of culture, the late stage of culture is that the form of a cell colony differs depending on each of the stages and it is desirable to set a target region according to the form.

Figure 3:
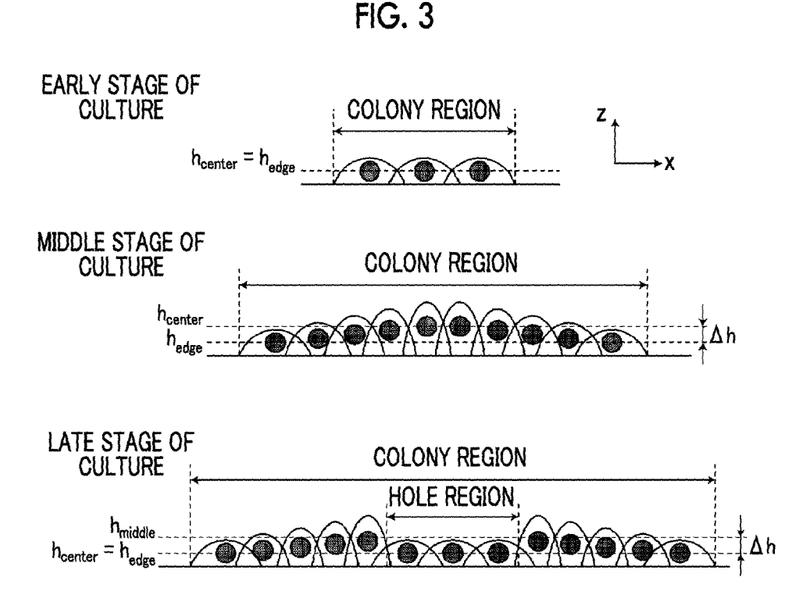
FIG. 3 is a diagram showing an example of the form of a stem cell colony in the early stage of culture, the middle stage of culture, and the late stage of culture.

Specifically, for example, in the case of a stem cell colony, in the early stage of culture, undifferentiated cells are uniformly distributed in a colony region example as shown in FIG. 3. Then, in the middle stage of culture, as shown in FIG. 3, undifferentiated cells are densely distributed in the central portion of the colony region, and differentiation starts and differentiated cells are distributed in the peripheral portion of the colony region.

Then, in the late stage of culture, as shown in FIG. 3, a phenomenon called a hole occurs in which differentiation occurs easily in the central portion of the colony region. Accordingly, differentiated cells are distributed in the central portion and the peripheral portion of the colony region, and differentiated cells are distributed in an intermediate portion between the central portion and the peripheral portion.

As described above, the form of the cell colony region changes in the early stage of culture, the middle stage of culture, and the late stage of culture. Therefore, in the present embodiment, a target region is set according to the form change. That is, a region to be imaged at high magnification is determined.

The information regarding the maturity of cells that is acquired by the maturity information acquisition unit 22 may be any information indicating the stage of maturity of cells. For example, a culture period measured by a timer or the like can be acquired as the information regarding the maturity. Without being limited to the culture period, for example, image information of the cell colony region in a low magnification image may be analyzed, the size of the cell colony, the number of cells in the stem cell colony, or the number of cells per unit area smaller than the stem cell colony may be measured, and such information may be acquired as the information regarding the maturity. For example, it is determined that the maturity increases as the measured number of cells increases. As the size of the cell colony, it is possible to acquire the area, perimeter, maximum diameter, and the like of the cell colony. In addition, the image information of the cell colony region may be acquired based on the position information of the cell colony specified by the colony region specifying unit 21. For the measurement of the number of cells in the cell colony, for example, it is preferable to detect each cell or the nucleus or nucleolus in the cell by pattern matching or the like and to count the number of detected cells.

In addition, for example, the brightness of the image of a cell colony region or a texture, such as uniformity or asperity, may be acquired as the information regarding the maturity. For example, in a case where cells to be imaged are stem cells, as the maturity increases, the density of stem cells increases, stem cells are further laminated, and the brightness of an image is gradually increased. Accordingly, it can be said that the maturity increases as the brightness increases.

In addition, in a case where the maturity increases and stem cells proliferate to be laminated as described above, the uniformity of the image becomes high, and a smooth image with a small amount of irregularities is obtained. Accordingly, it can be said that the maturity increases as the uniformity of an image becomes high and as the image becomes smooth. As a method of acquiring the feature quantity amount of the uniformity or smoothness of the image, it is possible to use a known method.

In addition, as the information regarding the maturity, the feature quantity of the shape of each stem cell colony may be acquired. As the maturity of the stem cell increases, the shape of the stem cell colony gradually approaches a circle. Then, differentiation in a peripheral portion progresses, and the complexity of the edge is increased. Therefore, such a feature quantity of change in the shape of the stem cell colony can be acquired as the feature quantity related to the maturity.

In addition, as the information regarding the maturity, the feature quantity of the thickness of each stem cell colony may be acquired. As the maturity of the stem cell increases, the stem cell colony becomes thick gradually. Therefore, such a feature quantity of the thickness of the stem cell colony can be acquired as the feature quantity related to the maturity. The thickness of the stem cell colony may be measured, for example, by a measuring device that is separately provided.

In addition, a user may set and input the information regarding the maturity described above using the input device 5, and the user may input not only the culture period or the size of a cell colony described above but also the passage number of cells as the information regarding the maturity.

In the present embodiment, the maturity of cells is divided into three stages. However, the maturity of cells may be divided into two stages or four stages or more without being limited to the three stages. As an interval of each stage, various intervals can be set according to the culture conditions or the like.

The target region determination unit 23 determines a target region in the cell colony based on the information regarding the maturity acquired by the maturity information acquisition unit 22 and the position of the colony region specified by the colony region specifying unit 21.

Figure 4:
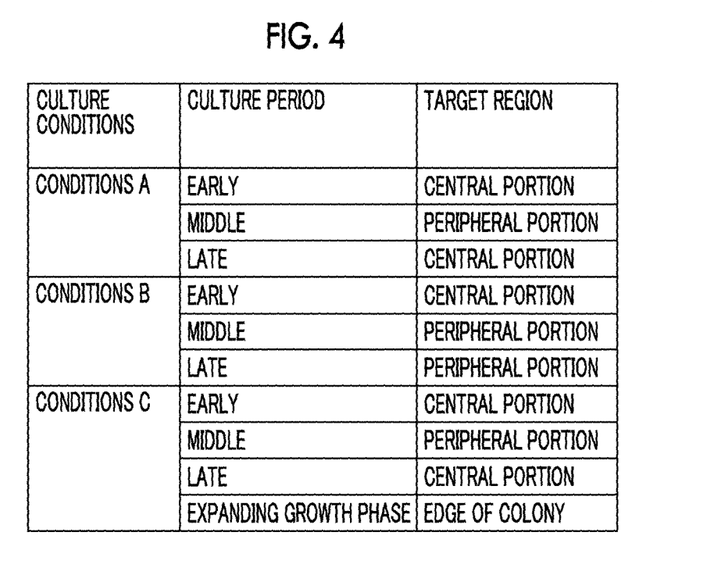
FIG. 4 is a diagram showing an example of a table in which culture conditions, a culture period, and the position of a target region are associated with each other.

Specifically, the target region determination unit 23 of the present embodiment has a table in which a culture period and a target region are associated with each other as shown in FIG. 4, and determines a target region with reference to the table. In the present embodiment, the target region determination unit 23 acquires not only the culture period but also the culture conditions, and determines a target region based on the acquired culture conditions and culture period with reference to the table shown in FIG. 4.

As the culture conditions, there are conditions regarding the type of the scaffolding or the medium, conditions regarding whether to use heterologous cells (feeder cells) that are different types from cells to be cultured, and the like. Even if the culture period is the same, the stage of the maturity differs depending on the culture conditions. Therefore, in the present embodiment, the culture conditions are also taken into consideration to determine the target region.

The culture conditions are not limited to the conditions described above, and may be any conditions as long as the conditions influence the growth rate of cells. For example, the environmental conditions of culture, such as temperature, humidity, or $CO_2$ concentration, may be included. The information of the culture conditions is set and input by the user using the input device 5, for example. However, for the temperature and the humidity described above, conditions measured by using a thermometer or a hygrometer may be used.

Figure 5:
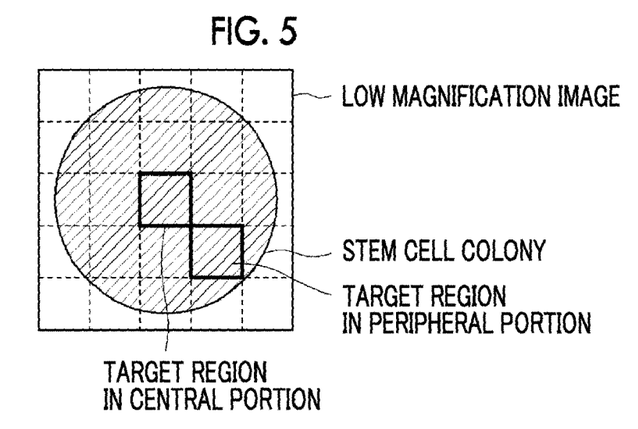
FIG. 5 is a diagram showing an example of a target region in a central portion and a target region in a peripheral portion of a cell colony.

Specifically, for example, in a case where the culture conditions are conditions A, the target region determination unit 23 sets a target region (rectangular region shown by a thick line) in a central portion as shown in FIG. 5 in order to mainly observe the state of undifferentiated cells. In a case where the culture period is the middle stage of culture, the target region determination unit 23 sets a target region in a peripheral portion as shown in FIG. 5 in order to observe how much the differentiation of undifferentiated cells has progressed. In a case where the culture period is the late stage of culture, the target region determination unit 23 sets a target region in the central portion again in order to observe the range of the hole described above. The range of the target region may be a range of each divided region obtained by dividing the imaging region of a low magnification image into a plurality of rectangular regions, for example, as shown in FIG. 5.

In addition, for example, in a case where the culture conditions are conditions B, unlike the case of the conditions A, in a case where the culture period is the late stage of culture, a target region is determined in a peripheral portion in order to observe how much the differentiation of undifferentiated cells has progressed.

As described above, the target region determination unit 23 determines a target region located at a position that changes with the stage of maturity. However, for the determination of a target region in which position and which stage, it is appropriately set depending on the state of cells or cell colonies that the user wants to observe.

In the above explanation, a region inferred to be likely to differentiate by the maturation of cells is determined as a target region by setting the central portion as a part to be observed in the early stage of culture, the peripheral portion as a part to be observed in the middle stage of culture, and the central portion as a part to be observed in the late stage of culture. However, as the region inferred to be likely to differentiate, not only the central portion or the peripheral portion described above but also a case is included in which, for example, the left half of a cell colony region is mature while maintaining the undifferentiated state and only the right half is differentiated. Accordingly, the region inferred to be likely to differentiate differs depending on the type or maturity of cells.

Therefore, it is preferable to appropriately set the region inferred to be likely to differentiate, as a target region, in consideration of the type or maturity of cells. The region inferred to be likely to differentiate may be set and input to the above-described table by the user, or may be automatically determined by analyzing the image of the cell colony region. For example, the density of cells may be calculated for each divided region in the cell colony region, and a region having a density equal to or less than a predetermined threshold value or a density equal to or greater than the threshold value may be determined as a region inferred to be likely to differentiate. The density of cells may be calculated by detecting individual cells or nucleus or nucleolus in each cell by pattern matching or the like as described above.

Without being limited to the density, a halo generated between individual cells may be detected, and a region having the area of the halo equal to or greater than a predetermined threshold value may be determined as a region inferred to be likely to differentiate. The halo is high-brightness artifacts caused by diffracted light passing through cells.

As the position of a target region, for example, an intermediate portion between a central portion and a peripheral portion may be set instead of the central portion or the peripheral portion of the colony region described above, and a target region may be determined in the intermediate portion.

Figure 6:
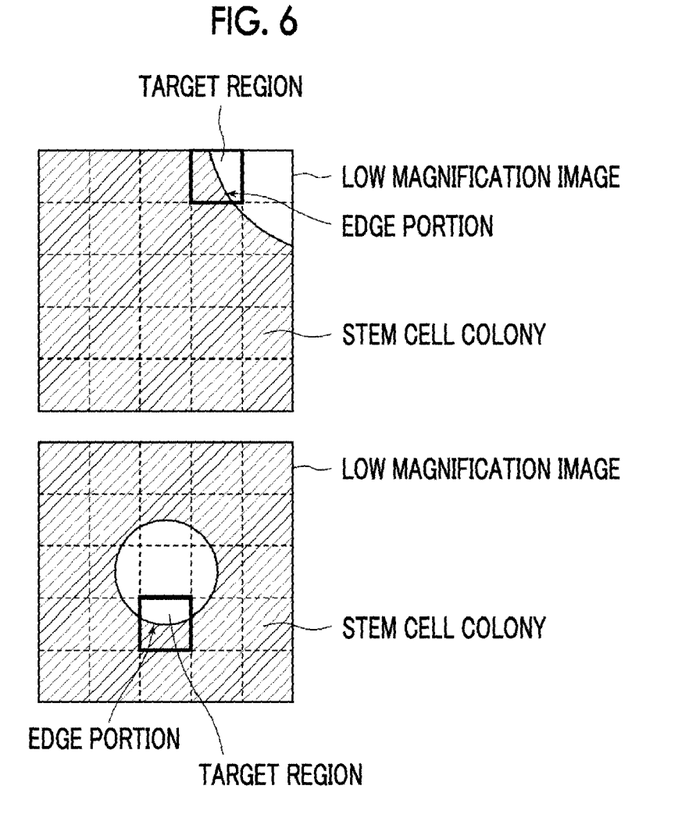
FIG. 6 is a diagram showing an example of a target region in the expanding growth phase.

In addition, for example, in a case where the maturity of the cell colony increases and the cell colony region does not fit in the imaging region of the low magnification image as shown in FIG. 6, the edge of the cell colony region may be detected, and a region including the edge may be determined as a target region. The upper diagram of FIG. 6 shows an example of the position of a target region in a case where the edge of a cell colony region is present in the upper right corner in the imaging region of a low magnification image, and the lower diagram of FIG. 6 shows an example of the position of a target region in a case where the edge of a cell colony region is present in the vicinity of the center of the imaging region of a low magnification image.

Specifically, for example, the stage of the expanding growth phase may be set as in the case of conditions C in the table shown in FIG. 4. In a case where the culture period is this stage, the edge of the cell colony region may be detected, and a region including the edge may be determined as a target region. The stage of the expanding growth phase may be determined from the culture period as described above, or may be determined by detecting that a circular region configured to include a number of cells is not extracted from the low magnification image.

Referring back to FIG. 1, the imaging control section 26 outputs a control signal to the control unit 12 of the cell culture device 1 based on the target region determined by the target region determination unit 23, and controls the movement of the stage 10 in the X-Y direction so that the target region in the cell colony is imaged at high magnification. In a case where the phase contrast microscope 3 is configured to be able to automatically change the magnification of the phase difference lens 34, the imaging control section 26 outputs a control signal so that the phase difference lens 34 of low magnification is changed to the phase difference lens 34 of high magnification. In a case where the phase contrast microscope 3 is configured to manually change the magnification of the phase difference lens 34, the user may perform a change to the phase difference lens 34 of high magnification at the time of high magnification imaging.

Then, high magnification imaging is performed in a state in which the position of the culture vessel 15 in the X-Y direction has been adjusted by the imaging control section 26 and the magnification of the phase difference lens 34 has been changed to high magnification. Accordingly, a high magnification image of the target region is captured.

The high magnification image acquisition unit 24 acquires the high magnification image that has been captured by the phase contrast microscope 3 as described above, and stores the high magnification image.

The display control section 27 displays a low magnification image or a high magnification image on the display 4.

The input device 5 includes a mouse, a keyboard, and the like, and receives an operation input from the user. For example, the input device 5 can receive the magnification when capturing a low magnification image or a setting input when capturing a high magnification image. The input device 5 receives a setting input of the culture conditions, the culture period, and the like that have been described above.

Figure 7:
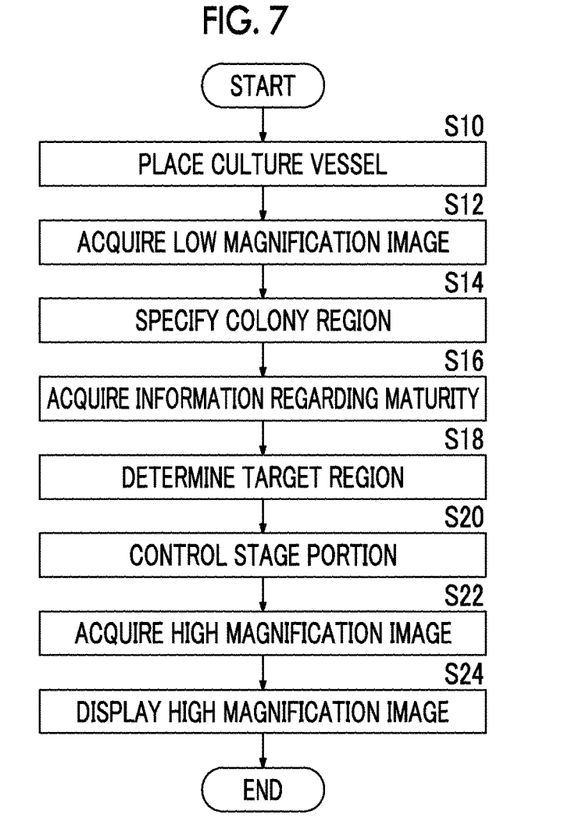
FIG. 7 is a flowchart illustrating the operation of the stem cell culture observation system using an embodiment of the cell image acquisition device of the present invention.

Next, the operation of the above-described cell culture observation system will be described with reference to the flowchart shown in FIG. 7.

First, in the cell culture device 1, the transport unit 11 selects a culture vessel to be imaged from a plurality of culture vessels housed therein, and places the selected culture vessel 15 on the stage 10 (S10).

Then, the magnification of the phase difference lens 34 of the phase contrast microscope 3 is set to low magnification and a low magnification image is captured, and the captured low magnification image is acquired by the low magnification image acquisition unit 20 (S12). The low magnification image acquired by the low magnification image acquisition unit 20 is output to the display control section 27, and is displayed on the display 4 by the display control section 27.

The low magnification image acquired by the low magnification image acquisition unit 20 is output to the colony region specifying unit 21, and the colony region specifying unit 21 specifies the position of a colony region in the low magnification image based on the input low magnification image (S14).

On the other hand, the maturity information acquisition unit 22 acquires information of culture conditions and information of the culture period as the information regarding the maturity of cells through a setting input or the like from the user (S16).

Then, the information of the culture period and the culture conditions acquired by the maturity information acquisition unit 22 is output to the target region determination unit 23. The target region determination unit 23 determines a target region, which is an imaging target in the high magnification imaging of the phase contrast microscope 3, based on the information of the culture period and the culture conditions and the position of the colony region, and outputs the result to the imaging control section 26 (S18).

Based on the position information of the target region determined by the target region determination unit 23, the imaging control section 26 moves the stage 10 in the X-Y direction so that the target region is imaged at high magnification (S20). At this time, the phase difference lens 34 in the phase contrast microscope 3 is changed to the phase difference lens 34 for high magnification imaging.

Then, in the phase contrast microscope 3, a high magnification image for detailed observation is captured in a state in which the focus position has been adjusted. The high magnification image captured by the phase contrast microscope 3 is acquired by the high magnification image acquisition unit 24 of the cell image acquisition device 2, and is output to the display control section 27 (S22). The display control section 27 displays the input high magnification image for detailed observation on the display 4 (S24).

According to the cell culture observation system of the embodiment described above, a target region in the colony region of a cell is determined based on the information regarding the maturity, and a high magnification image is acquired by imaging the target region at high magnification. Therefore, since it is possible to appropriately limit the target region according to the change in form of the colony region, it is possible to reduce the amount of data to be processed and stored.

In the cell culture observation system of the embodiment described above, a target region is determined based on the information regarding the maturity of cells and the culture conditions. However, depending on the type of cell, the way of its growth or the form change is different. Accordingly, the target region may also be determined by further taking the type of cell into consideration.

Specifically, for example, the table shown in FIG. 4 may be set for each type of cell, and the target region determination unit 23 may also acquire the information of the cell type to determine the target region. As the information of the cell type, there are pluripotent stem cells such as the iPS cells, the ES cells, or the STAP cells described above, cells of nerves, skin, or liver that are differentiation-induced from stem cells, and cancer cells. For example, the information of the cell type may be set and input by the user using the input device 5.

Specifically, it is thought that the distal end position of the blood vessel in a myocardial cell colony or a skin cell colony changes with a culture period, for example. Accordingly, a region including the distal end position of the blood vessel according to the culture period may be set as a target region.

In the cell culture observation system of the embodiment described above, the position of a target region in a cell colony is determined based on the information regarding the maturity of cells. However, according to the determined position of the target region, focus parameters in the focus control in the Z direction may be changed.

As described above, for example, in the case of a stem cell colony, in the early stage of culture, undifferentiated cells are uniformly distributed in a colony region example as shown in FIG. 3. Accordingly, the height $h_{center}$ of the nucleus of a stem cell in a central portion of the colony region is the same as the height $h_{edge}$ of the nucleus of a stem cell in a peripheral portion of the colony region.

Figure 8:
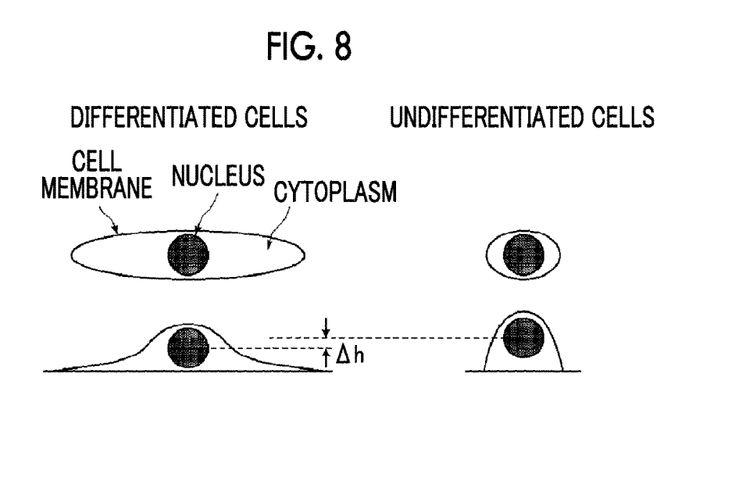
FIG. 8 is a diagram illustrating the ratio of nucleus/cytoplasm of undifferentiated cells and differentiated cells.

Then, in the middle stage of culture, as shown in FIG. 3, undifferentiated cells are densely distributed in the central portion of the colony region, and differentiation starts and differentiated cells are distributed in the peripheral portion of the colony region. FIG. 8 shows plan views (upper part of the figure) and elevation views (lower part of the figure) of undifferentiated cells and differentiated cells. Since the ratio of nucleus/cytoplasm in the differentiated cell is smaller than that in the undifferentiated cell, the height of the nucleus is low. Accordingly, as shown in FIG. 3, the height $h_{center}$ of the nucleus of the stem cell in the central portion of the colony region is larger than the height $h_{edge}$ of the nucleus of the stem cell in the peripheral portion of the colony region by $\Delta h$.

Then, in the late stage of culture, as shown in FIG. 3, a phenomenon called a hole occurs in which differentiation occurs easily in the central portion of the colony region. Accordingly, the height $h_{center}$ of the nucleus of the stem cell in the central portion of the colony region is the same as the height $h_{edge}$ of the nucleus of the stem cell in the peripheral portion of the colony region. However, the height $h_{middle}$ of the nucleus of a stem cell in an intermediate portion between the central portion and the peripheral portion is higher than the height $h_{center}$ and the height $h_{edge}$ by $\Delta h$.

As described above, the form of the cell colony region changes in the early stage of culture, the middle stage of culture, and the late stage of culture, and accordingly, the height of the nucleus changes with the position in the X-Y direction. Therefore, it is preferable to set the focus search initial position of the autofocus according to the position of the target region.

Figure 9:
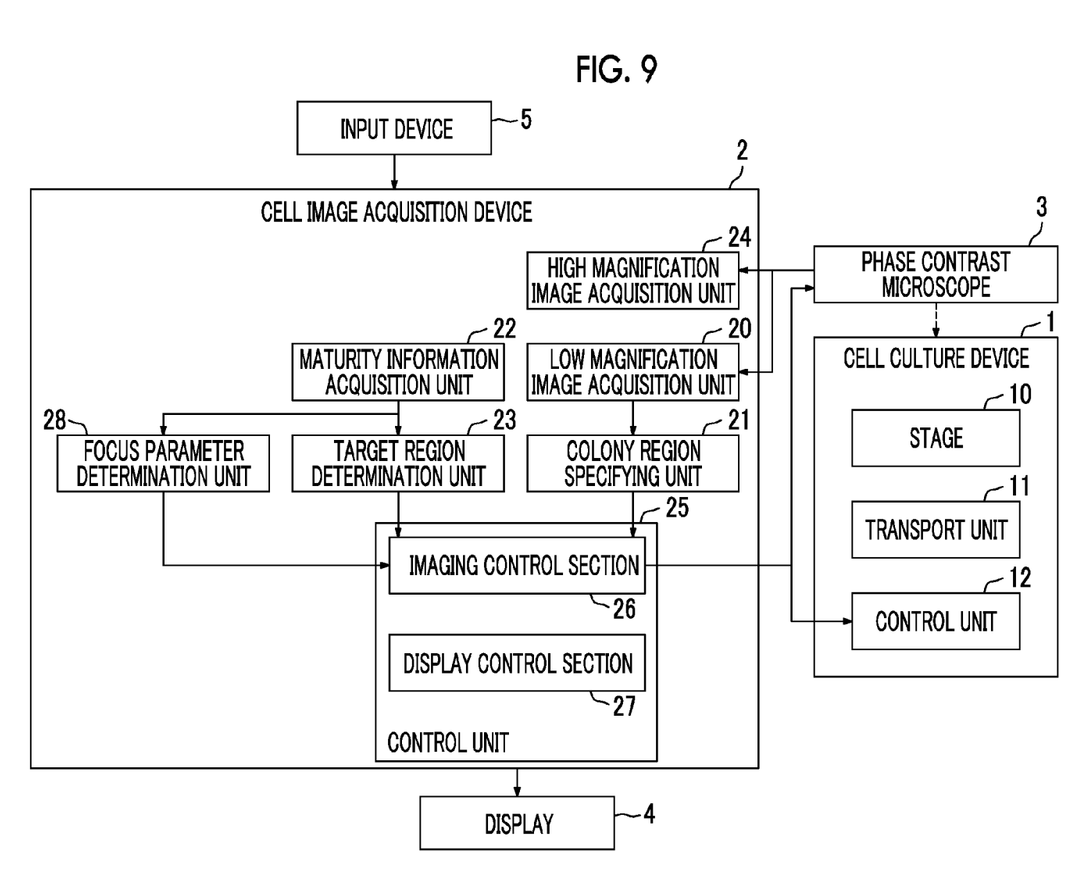
FIG. 9 is a diagram showing a modification example of the cell culture observation system shown in FIG. 1.

Accordingly, as shown in FIG. 9, a focus parameter determination unit 28 may be further provided, the focus parameter determination unit 28 may determine a focus search initial position according to the position of the target region, and the imaging control section 26 may control the autofocus in the phase contrast microscope 3 based on the determined focus search initial position.

Figure 10:
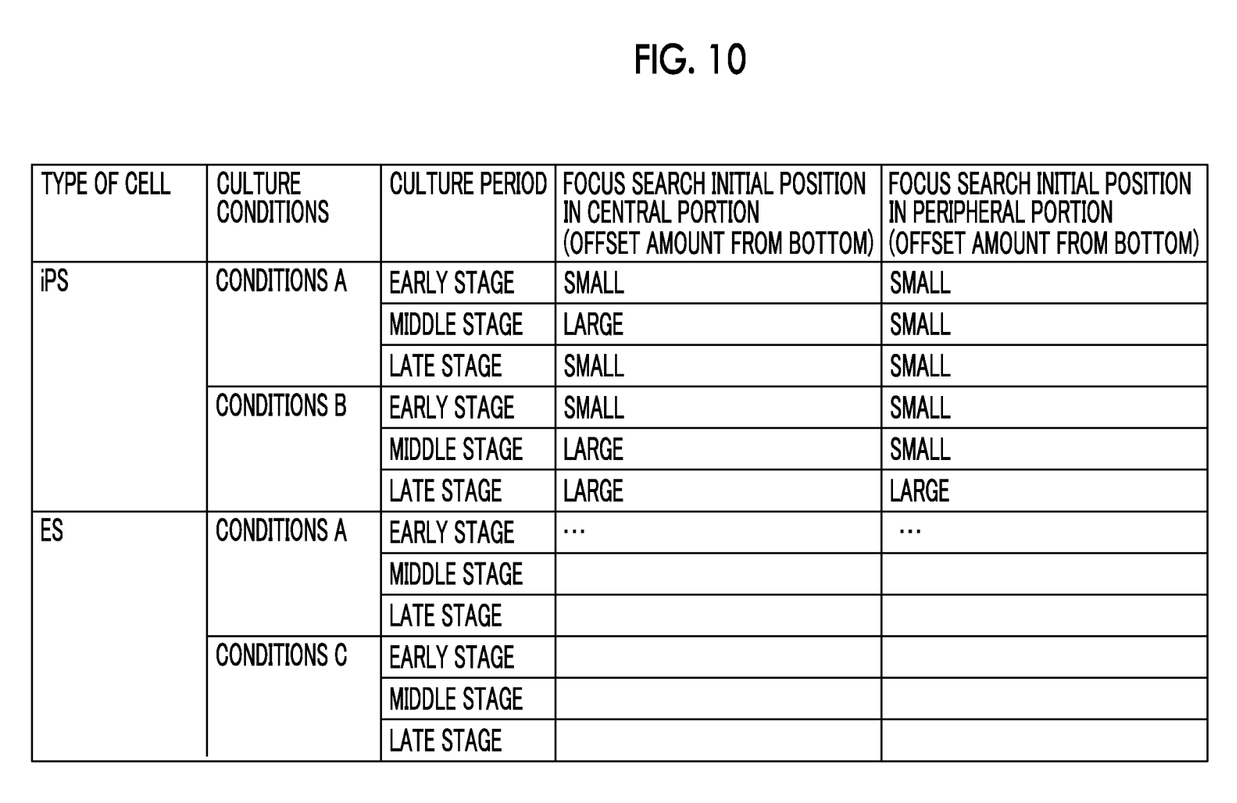
FIG. 10 is a diagram showing an example of a table in which the type of cell, culture conditions, a culture period, an observation position, and the focus search initial position of autofocusing are associated with each other.

Specifically, in the focus parameter determination unit 28, for example, a table shown in FIG. 10 is set in advance. The table shown in FIG. 10 is a table in which the type of cell, culture conditions, a culture period, a target position, and the focus search initial position of the autofocus are associated with each other. That is, the focus parameter determination unit 28 determines a focus search initial position in consideration of not only the position of a target region but also the type of cell, culture conditions, and the culture period. In the table shown in FIG. 10, the relative relationship of the offset amount (distance) from the bottom of the culture vessel 15 is shown as the focus search initial position. In practice, however, the absolute value of the offset amount is acquired, and the offset amount is determined as the focus search initial position. In the table shown in FIG. 5, the offset amount of ES cells is not shown although the offset amount of ES cells is actually set.

For example, in a case where the cell type information is an iPS cell, the information of culture conditions is conditions A, and the target region is a central portion of the cell colony region, the offset amount of the focus search initial position may be relatively reduced (brought closer to the cell mounting surface side) in a case where the culture period is the early stage of culture and the late stage of culture, and the offset amount of the focus search initial position may be relatively increased (away from the cell mounting surface) in a case where the culture period is the middle stage of culture.

Similarly, even if the cell type information is an iPS cell and the information of culture conditions is conditions A, in a case where the target region is a peripheral portion of the cell colony region, it is preferable to determine a relatively small offset amount without changing the offset amount according to the culture period.

Thus, by acquiring the offset amount with reference to the table shown in FIG. 10, it is possible to determine an appropriate focus search initial position according to the form of the target region.

In addition, a thickness for each position within the X-Y plane of the bottom of the culture vessel 15, thickness information for each position within the X-Y plane of the scaffold, and the like may be further acquired, and the focus search initial position may be determined by also taking these into consideration.

Although the method of determining the focus search initial position in the autofocus has been described above, the focus parameter determination unit 28 also determines a focus search range, a focus search width, a focus search order, the number of focus operations, and the like.

The focus search range is a change range of the focus position in the autofocus control, and has a lower limit and an upper limit. For the focus search range, for example, a table in which the type of cell and the focus search range are associated with each other may be set in advance, and a wider focus search range may be determined as the size of the cell becomes larger.

In addition, a table in which a target region in a cell colony region and a focus search range are associated with each other may be set in advance, and a focus search range corresponding to the position of the target region may be determined. In this case, for example, it is preferable to determine a relatively wide focus search range in a case where the target region is a central portion and to determine a relatively narrow focus search range in a case where the target region is a peripheral portion.

In addition, a table in which the culture period and the focus search range are associated with each other may be set in advance. In this case, for example, it is preferable to extend the focus search range as the culture period increases.

In addition, the focus search range may be determined for each combination of the type of cell, the position of a target region, and the culture period.

The focus search width is a change width at the time of one focus position change in the autofocus control. As the culture progresses to expand the cell colony, a variation in the density of cells may occur according to the location. Accordingly, in the focus search width that is set according to the early stage of culture in which a variation in the density of cells is small, a probability that the cell nucleus is out of the focus search range may be increased.

Therefore, for example, a table in which the culture period and the focus search width are associated with each other may be set in advance, and the focus search width may be made to extend as the culture period increases.

In addition, external force that each cell receives from surrounding cells is decreased toward the peripheral portion of the cell colony region. Accordingly, each cell is easy to move, and the variation increases more. Therefore, a table in which the position of a target region in a cell colony region and the focus search width are associated with each other may be set in advance, and the focus search width may be increased toward the peripheral portion of the cell colony region.

In addition, the focus search range may be determined for each combination of the position of a target region in a cell colony and the culture period.

As the focus search order, there are a case of performing autofocus control by sequentially changing the focus position from a high position to a low position with the bottom of the culture vessel 15 as a reference, a case of performing autofocus control by sequentially changing the focus position from the low position to the high position, and a case of performing autofocus control by alternately repeating a change in the focus position in a direction moving closer to the bottom of the culture vessel 15 and a change in the focus position in a direction away from the bottom of the culture vessel 15.

Since differentiated cells or cells around the colony are distributed to crawl on the bottom of the culture vessel 15 in many cases, it is efficient to search for the focus position from bottom side (low position) of the culture vessel 15. On the other hand, since undifferentiated cells or cells near the cell colony center stand in many cases, it is efficient to search for the focus position from a position away from the bottom of the culture vessel 15.

Accordingly, a table in which the position of a target region in a cell colony region and the focus search order may be set in advance, and the focus position may be searched for toward the high position from the low position for the central portion of the cell colony region and the focus position may be searched for toward the low position from the high position for the peripheral portion of the cell colony region.

In addition, as the culture progresses, a variation in the focus position increases as described above. For this reason, searching for the focus position from a position between the high position and the low position rather than searching for the focus position from one of the high position and the low position is believed to be efficient as a whole since the number of searches in the entire cell colony is reduced.

Accordingly, for example, a table in which the culture period and the focus search order are associated with each other may be set in advance, and the focus position may be searched for toward the high position from the low position as described above in the early stage of culture or the middle stage of culture, and the focus position may be searched for by alternately repeating a search of the focus position from the high position and a search of the focus position from the low position in the late stage of culture.

In addition, the focus search order may be determined for each combination of the position of a target region in a cell colony and the culture period.

The number of focus operations is an upper limit of the number of changes in the focus position in the autofocus control. In the early stage of culture to the middle stage of culture, in order to strictly recognize and evaluate the form of the cell nucleus or the equivalent tissue (for example, nucleolus), it can be said that strict focus accuracy is required. On the other hand, as the culture progresses, there is a tendency that the cell nucleus or the equivalent tissue is difficult to be visible due to differentiation or lamination of cells. In this case, it is believed that the strict focus accuracy is not required.

Therefore, for example, a table in which the culture period and the number of focus operations are associated with each other may be set in advance, and the number of focus operations may be made to decrease as the culture progresses. In contrast, there is also a case where there is a need to evaluate the expressed properties (chromatin condensation in the nucleus) as the culture progresses. In such a case, the focus accuracy may be increased by increasing the number of focus operations as the culture progresses.

In addition, a table in which the position of a target region in a cell colony region and the number of focus operations are associated with each other may be set in advance, and the focus accuracy of the central portion may be increased by increasing the number of focus operations toward the central portion rather than the peripheral portion of the cell colony region. In contrast, in a case where it is necessary to concentrate on the observation of the peripheral portion of the cell colony region, the focus accuracy of the peripheral portion may be increased by increasing the number of focus operations toward the peripheral portion rather than the central portion of the cell colony region.

In addition, the number of focus operations may be determined for each combination of the position of a target region in a cell colony and the culture period.

EXPLANATION OF REFERENCES

1: cell culture device
2: cell image acquisition device
3: phase contrast microscope
4: display
5: input device
10: stage
11: transport unit
12: control unit
15: culture vessel
20: low magnification image acquisition unit
21: colony region specifying unit
22: maturity information acquisition unit
23: target region determination unit
24: high magnification image acquisition unit
25: control unit
26: imaging control section
27: display control section
28: focus parameter determination unit
31: white light source
32: slit plate
33: objective lens
34: phase difference lens
35: objective lens
36: phase plate
37: imaging lens
38: imaging element

What is claimed is:

1. A cell image acquisition device, comprising:
   a processor configured to:
      acquire information regarding maturity of cells being cultured;
      acquire a cell image by imaging the cells at a first magnification and specify a colony region of the cells in the cell image;
      automatically determine a target region in the colony region of the cells based on information of a type of each of the cells and the information regarding the maturity of the cells being cultured,
      wherein the maturity is based on a density of the cells in the colony region, and
      wherein the information regarding the maturity is one of a plurality of stages during cell culture and the information regarding the maturity is acquired within the one of the plurality of stages during cell culture; and
      acquire a high magnification image by imaging the target region at a second magnification that is higher than the first magnification.

2. The cell image acquisition device according to claim 1, wherein the processor is further configured to determine the target region in a position that changes with a stage of the maturity of the cells.

3. The cell image acquisition device according to claim 2, wherein the processor is further configured to determine a region, which is inferred to be highly likely to differentiate due to maturation of the cells, as the target region.

4. The cell image acquisition device according to claim 3, wherein the processor is further configured to determine central portion in the colony region as the target region in a case where the maturity of the cells is a late stage.

5. The cell image acquisition device according to claim 3, wherein the processor is further configured to determine a region including an edge of the colony region as the target region in a case where a stage of the maturity is a stage of an expanding growth phase set in advance.

6. The cell image acquisition device according to claim 2, wherein the processor is further configured to determine a central portion in the colony region as the target region in a case where the maturity of the cells is an early stage, and determine a peripheral portion in the colony region as the target region in a case where the maturity of the cells is a middle stage that is a stage in which the early stage has progressed.

7. The cell image acquisition device according to claim 6, wherein the processor is further configured to determine a central portion in the colony region as the target region in a case where the maturity of the cells is a late stage.

8. The cell image acquisition device according to claim 6, wherein the processor is further configured to determine a region including an edge of the colony region as the target region in a case where a stage of the maturity is a stage of an expanding growth phase set in advance.

9. The cell image acquisition device according to claim 2, wherein the processor is further configured to determine a central portion in the colony region as the target region in a case where the maturity of the cells is a late stage.

10. The cell image acquisition device according to claim 9, wherein the processor is further configured to determine a region including an edge of the colony region as the target region in a case where a stage of the maturity is a stage of an expanding growth phase set in advance.

11. The cell image acquisition device according to claim 2, wherein the processor is further configured to determine a region including an edge of the colony region as the target region in a case where a stage of the maturity is a stage of an expanding growth phase set in advance.

12. The cell image acquisition device according to claim 1, wherein the processor is further configured to determine a region including an edge of the colony region as the target region in a case where a stage of the maturity is a stage of an expanding growth phase set in advance.

13. The cell image acquisition device according to claim 1,
wherein the processor is further configured to acquire the information regarding the maturity by analyzing image information of the colony region of the cells in the cell image.

14. The cell image acquisition device according to claim 13,
wherein the information regarding the maturity is information regarding a shape or a size of the colony region of the cells.

15. The cell image acquisition device according to claim 1,
wherein the processor is further configured to determine a target region in the colony region of the cells based on the information regarding the maturity and culture conditions of the cells.

16. The cell image acquisition device according to claim 1,
wherein the processor is further configured to determine at least one of a focus search initial position, a focus search range, a focus search width or a focus search order according to a position of the target region based on the information regarding the maturity during cell culture.

17. The cell image acquisition device according to claim 16,
wherein the processor is further configured to control autofocus in a microscope based on the determination of at least one of the focus search initial position, the focus search range, the focus search width or the focus search order.

18. The cell image acquisition device according to claim 1, wherein the processor is further configured to determine the target region based on an area of a halo generated between the cells.

19. The cell image acquisition device according to claim 1,
wherein the cell type is set by a user.

20. The cell image acquisition device according to claim 1, wherein the processor is further configured to determine at least one of a focus search initial position, a focus search range, a focus search width or a focus search order according to a position of the target region based on the information regarding the maturity during cell culture, and
wherein the focus search range is determined for each combination of a type of cell, a position of a target region, and a culture period.

21. A cell image acquisition method, comprising:
acquiring information regarding a maturity of cells being cultured;
acquiring a cell image by imaging the cells at a first magnification and specifying a colony region of the cells in the cell image;
automatically determining a target region in the colony region of the cells based on information of a type of each of the cells and the information regarding the maturity,
wherein the maturity is based on a density of the cells in the colony region, and
wherein the information regarding the maturity is one of a plurality of stages during cell culture and the information regarding the maturity is acquired within the one of the plurality of stages during cell culture; and
acquiring a high magnification image by imaging the target region at a second magnification that is higher than the first magnification.

22. A non-transitory computer readable recording medium recorded with a cell image acquisition program causing a computer to:
acquire information regarding a maturity of cells being cultured;
acquire a cell image by imaging the cells at a first magnification and specify a colony region of the cells in the cell image;
automatically determine a target region in the colony region of the cells based on information of a type of each of the cells and the information regarding the maturity of the cells being cultured,
wherein the maturity is based on a density of the cells in the colony region, and
wherein the information regarding the maturity is one of a plurality of stages during cell culture and the information regarding the maturity is acquired within the one of the plurality of stages during cell culture; and
acquire a high magnification image by imaging the target region at a second magnification that is higher than the first magnification.

* * * * *